United States Patent
Kim et al.

(10) Patent No.: US 6,809,084 B1
(45) Date of Patent: Oct. 26, 2004

(54) **COMPOSITIONS CONTAINING POLYSACCHARIDES FROM *PHELLINUS LINTEUS* AND METHODS FOR TREATING DIABETES MELLITUS USING SAME**

(75) Inventors: Hwanmook Kim, Taejon (KR); Sangbae Han, Cheongju-si (KR); Changwoo Lee, Taejon (KR); Kihoon Lee, Taejon (KR); Dongho Hong, Taejon (KR)

(73) Assignee: Korea Research Institute of Bioscience and Biotechnology, Taejon (KR)

( * ) Notice: Subject to any disclaimer, the term of this patent is extended or adjusted under 35 U.S.C. 154(b) by 0 days.

(21) Appl. No.: 10/149,117
(22) PCT Filed: Aug. 10, 2000
(86) PCT No.: PCT/KR00/00879

§ 371 (c)(1),
(2), (4) Date: Jun. 7, 2002

(87) PCT Pub. No.: WO01/60385
PCT Pub. Date: Aug. 23, 2001

(30) Foreign Application Priority Data

Feb. 15, 2000 (KR) .......................................... 2000/7137

(51) Int. Cl.[7] .................... A61K 31/715; A61K 31/726
(52) U.S. Cl. .............................. 514/54; 514/27; 514/8; 514/21; 514/866; 424/725
(58) Field of Search ................................. 514/54, 27, 8, 514/21, 866; 424/725

(56) References Cited

U.S. PATENT DOCUMENTS

| 4,801,582 A | * | 1/1989 | Hikino et al. .................. 514/54 |
| 6,420,348 B1 | * | 7/2002 | Kim et al. ..................... 514/54 |
| 2003/0086985 A1 | * | 5/2003 | Gupta et al. ................. 424/725 |

FOREIGN PATENT DOCUMENTS

| JP | 11-318432 | 11/1999 |
| KR | 101999-0081594 | 11/1999 |

* cited by examiner

Primary Examiner—James O. Wilson
Assistant Examiner—Devesh Khare
(74) Attorney, Agent, or Firm—Nath & Associates PLLC; Gary M. Nath; Lee C. Heiman

(57) ABSTRACT

The present invention relates to a novel use of polysaccharides (PL) from *Phellinus linteus* for treating diabetes mellitus, which provides medicine or food comprising polysaccharide as active components.

7 Claims, 5 Drawing Sheets

COMPOSITIONS CONTAINING POLYSACCHARIDES FROM *PHELLINUS LINTEUS* AND METHODS FOR TREATING DIABETES MELLITUS USING SAME

TECHNICAL FIELD

The present invention relates to a novel polysaccharide as an active component from *Phellinus linteus* for treating diabetes mellitus.

BACKGROUND ART

Diabetes mellitus and its complications are diseases with a high fatality rate in the world, together with cancer and cardiovascular diseases. According to a report issued by the National Commission on Diabetes, the fatality rate of diabetes is still continuously increasing. Diabetic patients, compared to normal persons, are highly susceptible to suffer from such complications as blindness, kidney disease and heart disease. Now, by the insulin therapy the acute or fatal symptoms of diabetes can be controlled, but the long-term complications reduce life expectancy.

Diabetes mellitus is classified into insulin-dependent diabetes mellitus (Type 1) and non-insulin-dependent diabetes mellitus (Type 2). Insulin-dependent diabetes mellitus is caused by damage of insulin-producing pancreatic beta cells, which leads to decrease of the amount of insulin and finally results in hyperglycemia.

Most insulin-dependent diabetes mellitus is the consequence of progressive beta-cell destruction during an asymptomatic period, often extending over many years. In the prediabetic period, circulating islet-cell autoantibodies and insulin autoantibodies may be detected. Insulin-dependent diabetes mellitus has been regarded as an autoimmune disease, and this hypothesis has been strengthened by the studies on the nonobese diabetic (NOD) mice and the BioBreeding (BB) rats. Both of these animals develop insulin-dependent diabetes mellitus spontaneously and their diabetic syndromes share many pathological features with that of humans with insulin-dependent diabetes mellitus. NOD mice, which can naturally fall into insulin-dependent diabetes mellitus, may usually start to expose the symptoms of diabetes in 12~14 weeks, and 80% of all mice have the symptoms. Immunocytes may be activated by unknown factors, and permeate into pancreatic ducts. In the islet, the immunocytes destroy beta cells and then bring about diabetes. Insulin acts on muscle, liver or fat cells to promote glucose metabolism and to lessen the level of glucose in blood. The diminution of insulin in blood by destruction of beta cells leads to deactivation of glucose metabolism in muscle or liver cell, resulting in diabetes mellitus. It has been reported in many studies that beta cell antigen, macrophages, helper T cells, cytotoxic T cells (CTLs), and the like are concerned with the outbreak of diabetes mellitus, and that oxygen free radicals or cytokines from inmiunocytes are responsible for destruction of beta cells.

Polysaccharide (PL) is a substance isolated from *Phellinus linteus*. Extraction of PL has been already disclosed (Chem. Pharm. Bull., 43(12), 2105–2108, 1995). PL can be extracted by the methods such as hydrothermal extraction, ethanol extraction method, DEAE-cellulose chromatography, and gel-permeation chromatography. PL comprise of 13.2% proteins and 82.5% saccharides, wherein 6.8% of the saccharides is uronic acid. MW of PL is definitely 153 KD, determined by gel-permeation chromatography. It was confirmed from neutral glucose composition analysis that PL consists of 7.0% of Ala, 3.7% of Xyl, 21.1% of glucose, 24.1% of Gal and 44.2% of Man, and from gas chromatography that uronic acid is a glucuronic acid 10 kinds of amino acids have been found in PL and Asp and Glu are major constituents. Saccharide parts and complete structure of PL play an important role on physiological activity of PL, but its protein parts are less significant. It has been found out that PL is polymer comprising O-type linkage (Chem. Pharm. Bull., 44(5), 1093–1095, 1996) and that PL is an immunoregulator for immunological enhancement (Int. J. Immunopharmacol 18(5), 295–303, 1996). PL improves entirely immune response. It has been confirmed by cell experiment and animal test that PL enhances the immunological function of T cells, macrophages, NK cells and B cells. Immunological enhancement of PL is effective to suppression of cancer growth or metastasis (Immunopharmacol, 41, 157–164, 1999). PL controlled the growth and transference of animal's cancer cell, B16F10, and the growth of human solid cancer cell, NCI-H23.

Diabetes research has been directed toward prevention and cure of insulin-dependent diabetes mellitus. Studies on prevention of insulitis and treatment of diabetes has mainly utilized the experimental models of diseases in laboratory animals such as NOD mice, and most therapeutic strategies for treatment of diabetes mellitus are directed to suppression and regulation of autoimmune response in order to prevent beta-cell destruction. Autoimmune disease, insulin-dependent diabetes mellitus results from increasing abnormalities of cellular immunity.

Various immunotherapies for preventing destruction of pancreatic beta-cells have been attempted. Neonatal thymectomy is the method of suppressing the outbreak of diabetes mellitus in NOD mice by killing T lymphocytes. Also, it has been known that depletion of macrophages or T cells using antibodies to T cell-dependent antigens represses diabetes. Some reports discloses that diabetes mellitus can be prevented by controlling production and reaction of free radical, for example, NO released from immunocytes by antioxidants such as nicotinamide, vitamin E, probucol, MDL29311, and U78518F, as has been reported.

To date, researches on immunosuppressive therapy are continued. However, treatment of diabetes mellitus utilizing glucocorticoids and cyclophosphamide has proved to be largely unsuccessful. Although studies on the use of cyclosporin A, rapamycin, and FK506 in diabetes appear to be encouraging, generalized immunosuppression involves potential complications including infections and drug-induced kidney and liver damage. Furthermore, curing with long-term administration can occasionally induce cancer. Studies on immunosuppressive therapy for diabetes mellitus is progressing, and the suppression of diabetes of NOD mice using cytokines such as IL-4 and IL-10 has been reported. Also, such immuno-regulatory agents as OK-432, LZ-8, BCG, and CFA have been reported to control diabetes mellitus of NOD mice, but their mechanism has yet to be established.

The present inventors achieved this invention, proving that polysaccharides (PL) from *Phellinus linteus* prevent destruction of pancreatic beta-cells, resulting in prevention and cure of diabetes mellitus.

DISCLOSURE OF THE INVENTION

The present invention provides a novel use of polysaccharide (PL) as active components from *Phellinus linteus* for treating diabetes mellitus.

The purpose of this invention was achieved by demonstrating effects of PL on prevention and cure of diabetes mellitus by administering PL from *Phellinus linteus* to NOD mice; examining inhibition of production of cytokine and suppression of streptozotosin-induced diabetes; and confirming that the diabetes-suppressing effect of PL originates from its selective regulation of immune response like above mentioned manners.

The present invention consists of following steps:

the step of comparing the urine glucose level of PL-injected NOD mice with that of control group, not receiving PL, in order to verify the diabetes-suppressive effect of PL from *Phellinus linteus*;

the step of observing the transition of pancreatitis to insulitis in PL-injected NOD mice, comparing to the case of control group, to verify the insulitis-suppressive effect of PL;

the step of measuring the expression level of cytokine MRNA in the separated spleen of NOD mice after a two-day intraperitoneal injection of the inventive PL, to confirm the diabetes-suppressive activity of PL based on its regulation of the cytokine production;

the step of transplanting lienal cells of non-PL-injected mice to NOD.Scid mice and measuring the occuring level of diabetes, to confirm that the inventive PL regulates immune responses and suppresses the outbreak of diabetes;

the step of checking it by analyzing difference between the blood glucose level of ICR mice with and without intraperitoneal injection of streptozotocin that PL cannot inhibit the beta cell destruction by streptozotocin, to confirm that the inventive PL has selective regulation of immune, responses resulting in suppression of diabetes mellitus; and the step of examining their weight and mortality to investigate the side effects of PL on NOD mice.

Doses of the inventive PL were 100 mg/kg/day every other day with intraperitoneal injection. The dose level, route, and schedule of administration, however may vary depending on the condition of the subject.

PL suppressed completely crisis of diabetes mellitus of NOD mice. Prevention and cure of diabetes mellitus by PL was examined by the test, in which the urine or blood glucose level had been compared to that of control and significant drop was observed. PL inhibited lymphocyte infiltration into pancreatic ducts, to suppress insulitis.

Activation of T lymphocytes and macrophages plays an important role in autoimmune disease system. IL-2 and IFN-gamma, which are cytokine from Th1 cells, enhance autoimmune responses. IL-2 promotes destruction of beta cells by activating cytotoxic T cells (CTLs). IFN-gamma can activate macrophages, and the activated macrophages amplify the antigen presenting function to increase autoimmune responses. Simultaneously, free radicals such as activated oxygen may be increased, resulting in destruction of beta cells. Increase of IL-10 or IL-4 cytokine expression by cytokines from Th2 leads to inhibition of function of Th1 cell and consequently decline in autoimmune responses. IL-6 and IL12 are cytokines expressed by macrophages. Particularly, IL-12, which stimulates Th1 cells to enhance the production of IL-2, performs an important function in inducing autoimmune diseases such as diabetes mellitus. PL inhibited expression of such cytokines as IL-2, IFN-gamma, IL-10, IL-6 or IL-12, which play an important part in the occurrence of diabetes mellitus. Although the increment of secretion of IL-4 from Th2 is thought to have been a significant reason of the decline of Th1 cell function, nothing is supposed to do with decrease in the expression of IL-10. PL's regulating function works as a major factor of suppressing diabetes mellitus.

The important feature of this invention is that PL has a curing effect on diabetes mellitus without any negative effect. Since NOD mice receiving PL showed no drop of their weight and were never led to death, PL is expected to have no side effect.

Insulin-dependent diabetes mellitus can be induced by streptozotocin. Streptozotocin destroys selectively pancreatic beta cells, and diabetes mellitus induced by streptozotocin is similar with diabetes naturally occurring in NOD mice. NOD mice mediate the autoimmune responses to break the beta cells, whereas streptozotocin does not do that. PL could not suppress the destruction of beta cells occurring by streptozotocin. This result shows PL is a substance which regulates selectively the immune responses to suppress the outbreak of diabetes mellitus.

NOD mice are the best disease animal models in studies on insulin-dependent diabetes. NOD mice can naturally fall into insulin-dependent diabetes mellitus and the symptoms are very similar with those of human. The effects of PL on preventing and treating of diabetes were proved with NOD mouse model and following examples is presenting more detailed description.

EXAMPLES

The following examples are offered to illustrate this invention and are not meant to be construed in any way as limiting the scope of this invention.

Example 1

Prevention and Cure of Clinical Diabetes by Administration of PL

Figure 1:
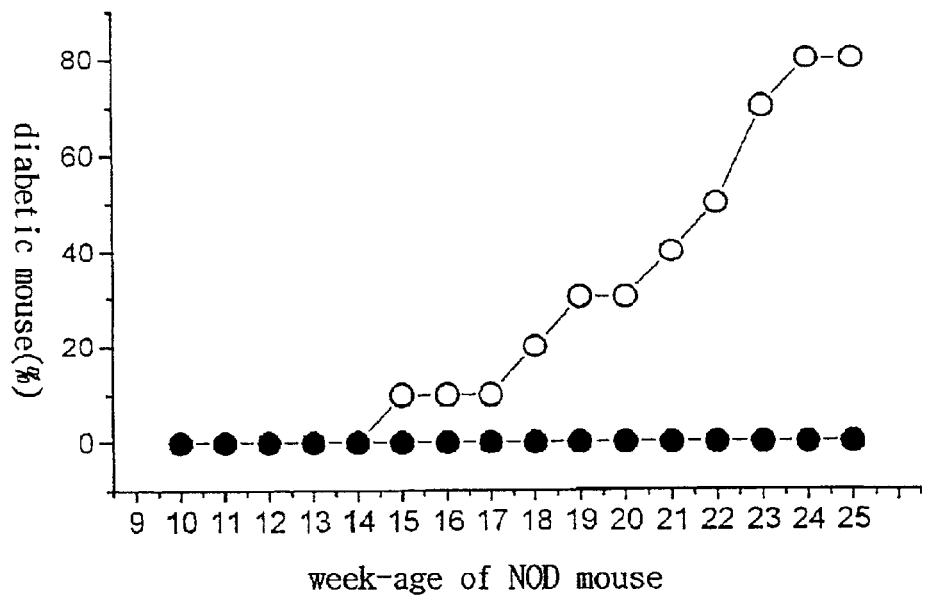
FIG. 1 shows prevention and cure of diabetes mellitus by administrating PL. Diabetic mice were selected according to the urine glucose level, and the percentage is based on the total mice (10 head). Open circles (○) are of control NOD mice and closed circles (●) are of NOD mice receiving PL.
Figure 2:
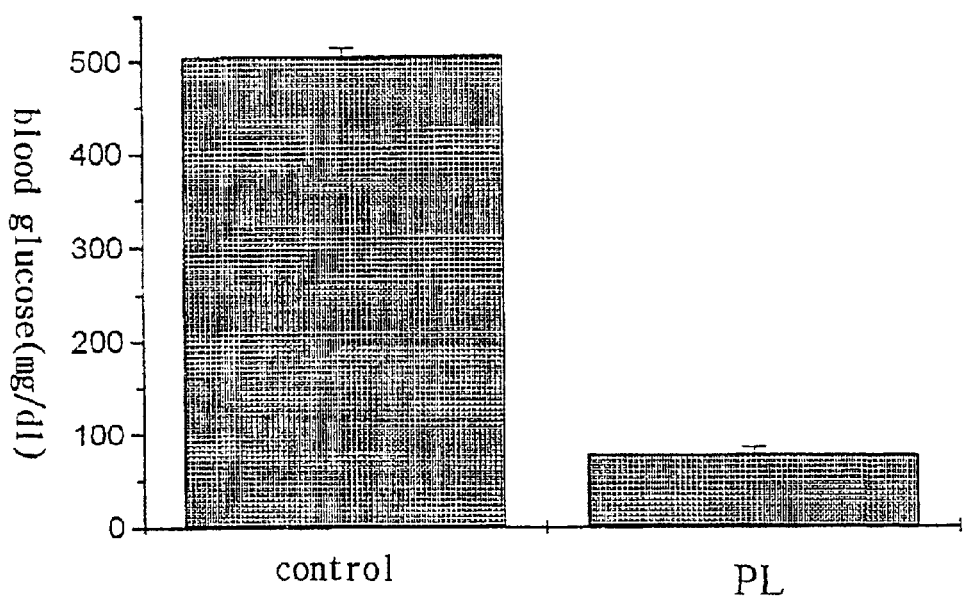
FIG. 2 illustrates decrease of blood glucose by administration of PL. After we isolated plasma from NOD mouse, the blood glucose was measured with the blood biochemical analyzer (Cibacorning, USA).

PL was intraperitoneally injected in 100 mg/kg from 8 weeks to 24 weeks of age, and the urine glucose was measured with uropaper (Eiken Chemical Co. Ltd., Japan) every week. In control group of NOD mice, not receiving PL, the urine glucose was first detected from 15 weeks of age, and at 24 weeks, 80% of the mice had the urine glucose detected (FIG. 1). Experimental group of NOD mice with administration of PL didn't have the urine glucose detected, and these results show complete suppression of clinical diabetes by administration of PL. Average blood glucose of non-PL-injected NOD mice was 500 mg/dl, which means diabetes mellitus crisis, and that of PL-injected NOD mice was 100 mg/dl, which means the normal condition (FIG. 2). Consequently, it was proved that PL could prevent clinical diabetes in NOD mice completely.

Example 2

Suppression of Insulitis by Administration of PL

Figure 3:
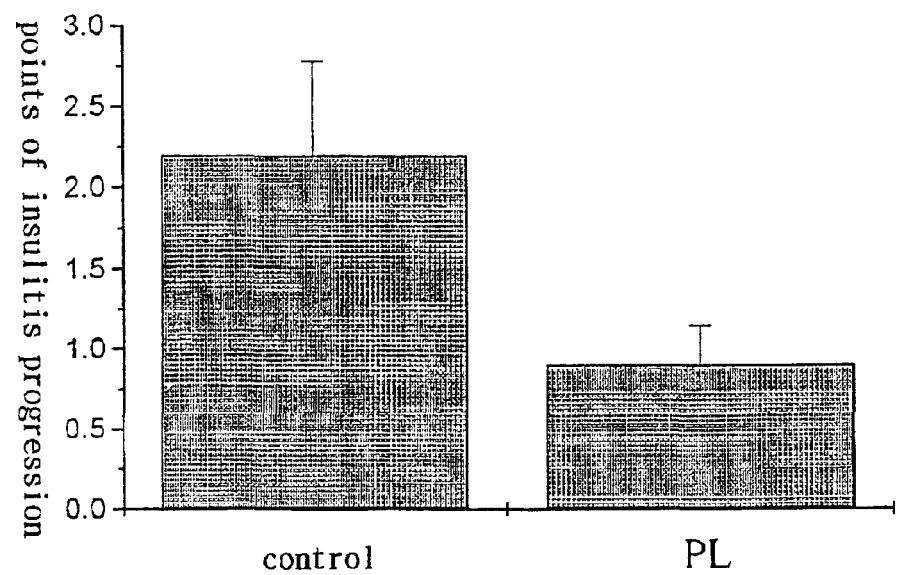
FIG. 3 illustrates decline of insulitis by administration of PL.
Figure 4:
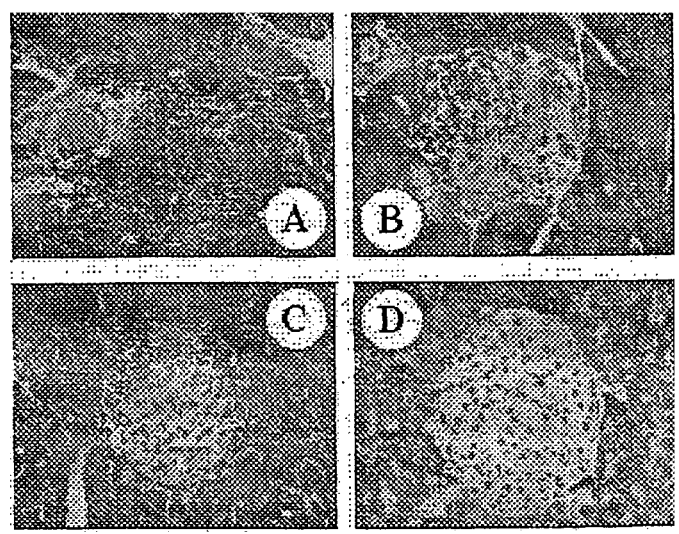
FIG. 4 illustrates decline of insulitis by administration of PL. Control NOD mice (A) suffered from severe insulitis, but NOD mice receiving PL (B, C, D) had their insulitis decreased.

In insulin-dependent diabetes mellitus, insulitis may be induced by lymphocyte infiltration into pancreatic ducts and destruction of beta cells thereby. Macrophages and T cells are the major infiltrating lymphocytes, and these immune cells destroy beta cells. The pancreas from both the PL-injected and the non-injected NOD mice were preserved in formalin and to preparation. After staining with hematoxylin/eosin, the lymphocyte infiltration level was measured. 1, 2, and 3 point were respectively given to 25, 50, and 75% of insulitis progression, and the average value of insulitis progression was calculated (FIG. 3). The NOD mice, not receiving PL had more than 2 point, or over 50% of infiltration, while the infiltration level of the PL-injected mice was less than 1 point, or under 20% of infiltration. This result showed that PL could suppress the lymphocyte infiltration into pancreatic ducts to debilitate insulitis. FIG. 4 shows the result of pathological tests: A indicates the condition of insulitis of non-PL-injected mice, showing that most of pancreatic ducts were infiltrated by lymphocytes; B, C, and D show that lymphocyte infiltration was reduced by administration of PL. This experiment demonstrated that PL suppresses insulitis, resulting in prevention of occurrence of diabetes mellitus.

Example 3

Inhibition of Cytokine Production by PL

Figure 5:
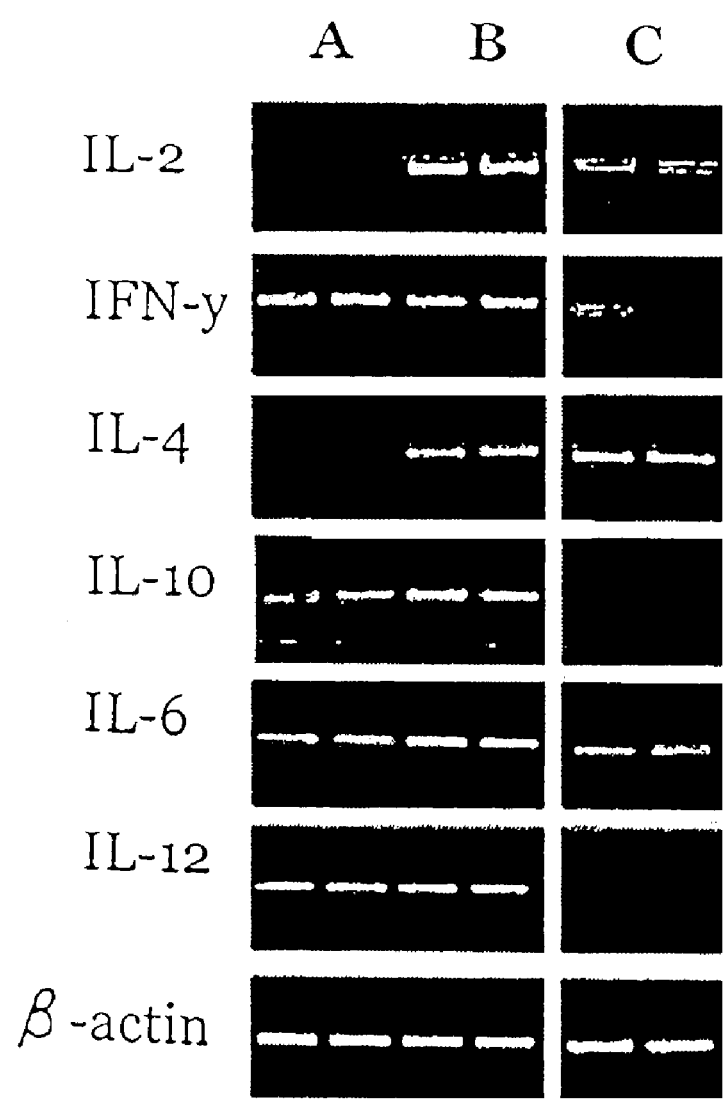
FIG. 5 shows change of expression pattern of lymphocyte's cytokines by administration of PL. A is of 6-week-old NOD mouse without diabetes, B is of 11-week-old NOD mouse with diabetes, and C is of 11-week-old NOD mouse receiving PL.

Th cells and macrophages have been known to play an important role in the pathogenesis of diabetes mellitus. According to unknown mechanism, macrophages are activated, and the activated cells produce IL-12. Then IL-12 activates Th1 cells to promote production of IL-2 and IFN-gamma, and these cytokines activate CTLs and macrophages. The activated CTLs and macrophages destroy beta cells and reduce production of insulin, resulting in occurrence of diabetes mellitus. In this manner, beta cells are disrupted through multi-steps of various mechanisms. Cytokines have a significant part in these immune responses, and control of cytokine production is expected to be the prevention and cure of diabetes mellitus. FIG. 5 illustrates the change of cytokine expression of lymphocytes by PL. PL was intraperitoneally administered to NOD mice from 8 weeks age every other day. In lienal cells from 11-week-old mice, the cytokine mRNA expression level was measured using RT-PCR (the reverse transcription polymerase chain reaction). A is of 6-week-old mouse, B is of 11-week-old one, and C denotes the cytokine expression of 11-week-old mouse receiving PL. 6-week-old one is of normal condition without the symptoms of diabetes or insulitis, and 11-week-old one is of starting point of insulitis. In other words, the 11-week-old mouse is in the situation that the immunologic functions are abnormally activated and lymphocyte infiltration is started. At the age of 11 weeks when the functions are brisk, the immunologic functions of mouse's lien cells and their regulation by PL were measured. In 11-week-old mouse, MRNA expression of IL-2, IL-10, and IL-6 increased intensively, and by administration of PL, the expression of IL-2, IFN-gamma, IL-10, IL-6, and IL-12 was strongly suppressed. As you see, the drop of cytokine production results in suppression of its autoimmune responses to beta cells, to cure diabetes mellitus. IL-4 and IL-10 expressed by Th2 cells can weaken the cell function of Th1 cells. The increased expression of IL-4 by PL was assumed to inhibit Th1 cell function relating to occurrence of diabetes mellitus. However, the reason of the difference between the expression of IL-10 and that of IL-4 has not been proved. From above results, it becomes clear that PL regulates the cytokine production of lymphocytes, resulting in suppressing the occurrence of diabetes mellitus.

Example 4

Test of Transplantation to NOD.Scid Mouse

Figure 6:
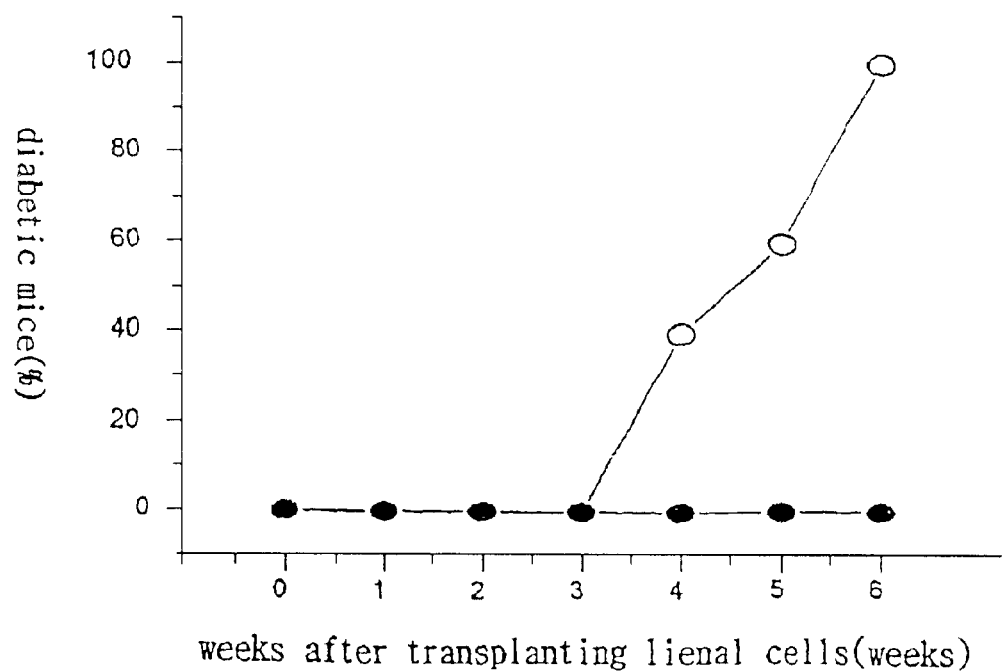
FIG. 6 illustrates the occurring level of diabetes mellitus in transplanting lienal cells from NOD mice to NOD.Scid mice (Open circles (○) are of the transplant group of lienal cells of NOD.Scid mice with diabetes crisis, and closed circles (●) are of the transplant group of lienal cells of NOD mice with PL).

To examine that prevention and cure of insulin-dependent diabetes by PL is the result of its regulation of immunologic reactions, the test of transplantation to NOD.Scid mouse was performed. NOD.Scid mouse is a mouse without T lymphocytes, so never suffer from diabetes. The lienal cells from NOD mice used in Example 1 were transplanted to NOD.Scid mice, and symptoms of diabetes mellitus were observed. All of the NOD.Scid mice, which the lienal cells of the 25-week-old NOD mice receiving no PL of the mice in Example 1 had been transplanted to, fell into some symptoms of diabetes mellitus after 6 weeks (FIG. 6). This result shows that T cells in the transplanted lienal cells destroyed beta cells of NOD.Scid mice to cause diabetes mellitus, and consequently proves that diabetes mellitus in NOD mouse is induced by immune responses or immunologic reactions. NOD.Scid mice, which the lienal cells of NOD mice receiving PL had been transplanted to, didn't show the symptoms of diabetes. This result confirmed that PL regulates immunologic responses to suppress disruption of beta cells by T cells.

Example 5

Effects of PL on the Streptozotocin-induced Diabetes

Figure 7:
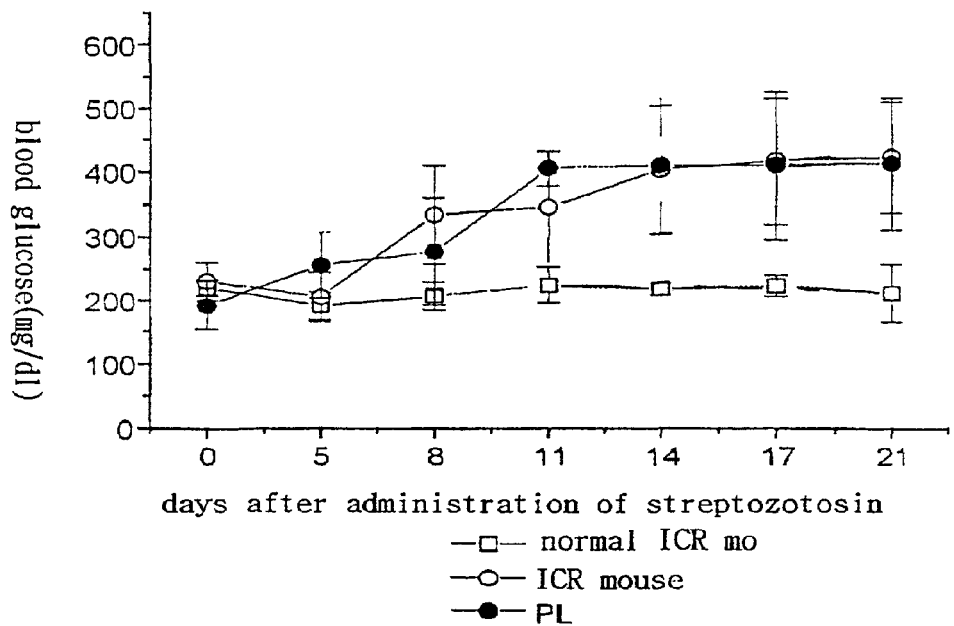
FIG. 7 illustrates the effect of PL on experimental group with streptozotocin-induced diabetes. Blood glucose values were measured with Accutrend sensor system (Boehringer Mannheim, Germany).
Figure 8:
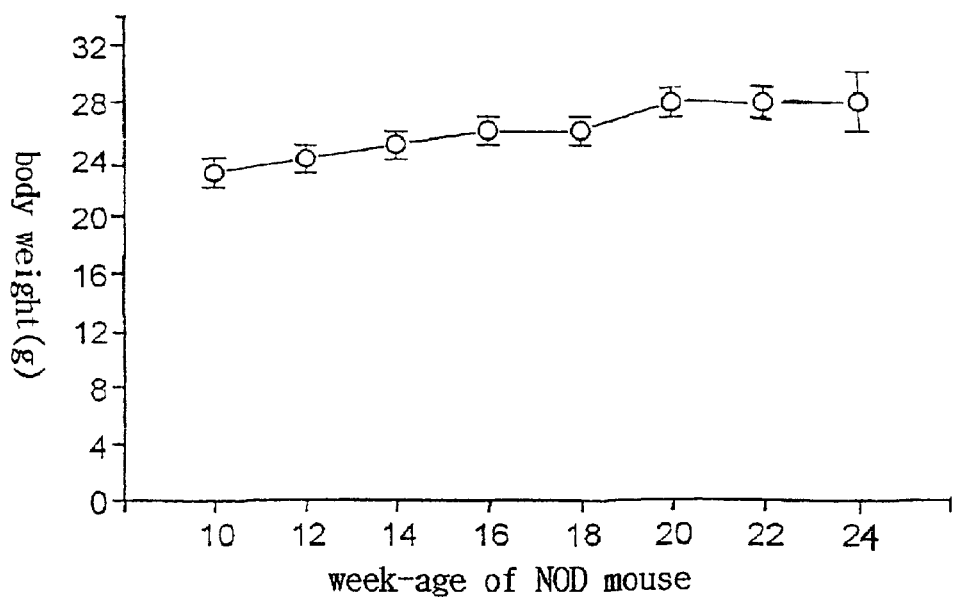
FIG. 8 shows that PL has no side effect. NOD mice receiving PL showed no drop of their weight and were never led to death.

Streptozotocin, which can induce Insulin-dependent diabetes mellitus, destroys selectively pancreatic beta cells, and diabetes mellitus induced :by streptozotocin is similar with diabetes naturally occurring in NOD mice. NOD mice mediate the autoimmune responses to break the beta cells, whereas streptozotocin does not do that. ICR mouse received 60 mg/kg of streptozotocin three times with intraperitoneal injection. Streptozotocin was used in solution of citrate buffer (pH 4.2, 4° C.). The blood glucose level of ICR mouse treated with streptozotocin was 450 mg/dl, whereas that of normal ICR mouse without streptozotocin was 200 mg/dl (FIG. 7). PL couldn't inhibit the destruction of beta cells by streptozotocin. This result proves that PL cannot suppress the destruction of beta cells by chemical compounds, but can suppress diabetes mellitus of NOD mouse by regulating selectively immune responses.

Example 6

Side Effects of PL

In NOD mice receiving PL from 8 weeks to 24 weeks age, their weight and mortality were checked in order to examine the negative effect of PL. Since NOD mice receiving PL showed no drop of their weight and were never led to death, PL is proved to have no side effect.

INDUSTRIAL APPLICABILITY

Through the aforementioned examples, it has been addressed that PL is a therapeutic agent for prevention and cure of diabetes mellitus by suppressing destruction of beta cells. Therefore, PL in the present invention is greatly useful for the medical and pharmaceutical industries relating to prevention and cure of diabetes mellitus.

What is claimed is:

1. A composition comprising a polysaccharide substance (PL) as an active component from *Phellinus linteus* for treating diabetes mellitus, wherein the polysaccharide substance has the following features:
   (a) said polysaccharide substance comprises 13.2% proteins and 82.5% saccharides, wherein 6.8% of the saccharides are uronic acid with Glc bound;
   (b) molecular weight of PL is 153 KD; and
   (c) the neutral sugar composition of the PL consists of 7.0% Ara, 3.7% Xyl, 21.1% Glc, 24.1% Gal, and 44.2% Man.

2. The composition of claim 1, wherein the composition further comprises a pharmaceutically acceptable carrier.

3. A method for treating diabetes mellitus in a patient in need thereof, comprising administering to the patient a therapeutically effective amount of the composition of claim 1.

4. The method of claim 3, wherein said diabetes mellitus is insulin-dependent diabetes mellitus.

5. The method of claim 3, wherein the PL is administered to said patient in an amount of about 100 mg per kg of body weight.

6. The method of claim 3, wherein said composition is administered to said patient via intraperitoneal injection.

7. The method of claim 3, wherein said composition is administered to said patient every other day.

* * * * *